US006788405B2

(12) United States Patent
Hunt

(10) Patent No.: US 6,788,405 B2
(45) Date of Patent: Sep. 7, 2004

(54) NONLINEAR OPTICAL SYSTEM FOR SENSING THE PRESENCE OF CONTAMINATION ON A SEMICONDUCTOR WAFER

(75) Inventor: Jeffrey H. Hunt, Chatsworth, CA (US)

(73) Assignee: The Boeing Company, Chicago, IL (US)

( * ) Notice: Subject to any disclaimer, the term of this patent is extended or adjusted under 35 U.S.C. 154(b) by 206 days.

(21) Appl. No.: 10/167,872

(22) Filed: Jun. 12, 2002

(65) Prior Publication Data

US 2003/0231302 A1 Dec. 18, 2003

(51) Int. Cl.[7] .............................................. G01N 21/88
(52) U.S. Cl. .............................. 356/237.4; 356/237.5; 356/237.2; 356/309; 250/559.4
(58) Field of Search ................ 356/237.1, 237.2–237.6, 356/600, 239.1–239.8, 317–334; 250/559.4, 559.41

(56) References Cited

U.S. PATENT DOCUMENTS

| | | |
|---|---|---|
| 5,294,289 A | 3/1994 | Heinz et al. |
| 5,623,341 A | 4/1997 | Hunt |
| 5,875,029 A | 2/1999 | Jann et al. |
| 5,883,714 A | 3/1999 | Jann et al. |
| 5,898,499 A | 4/1999 | Pressesky |
| 5,923,423 A | 7/1999 | Sawatari et al. |
| 5,973,778 A | 10/1999 | Hunt |
| 6,317,514 B1 | 11/2001 | Reinhorn et al. |
| 6,359,451 B1 | 3/2002 | Wallmark |

OTHER PUBLICATIONS

"Light Waves at the Boundary of Nonlinear Media"—The Physical Review, 128, Pag 193, 1962, Bloembergen and P.S. Pershan.
"Surface Studies by Optical Second Harmonic Generation: an Overview"—Journal of Vacuum Science and Technology B, vol. 3, No. 5, Sep. Oct. 1985, pp. 1464–1466, Y.R. Shen.

Primary Examiner—Richard A. Rosenberger
Assistant Examiner—Vincent P. Barth
(74) Attorney, Agent, or Firm—Shimokaji & Associates, P.C.

(57) ABSTRACT

First and second laser inputs are directed to a location on a semiconductor wafer to be interrogated. A first signal analyzer receives a first light signal at a first second-harmonic wavelength generated by the first laser input and converts the signal to a first electronic signal, thus monitoring the intensity of the first second-harmonic wavelength as a function of contamination. A second surface optical signal analyzer provides a similar function at a second second-harmonic wavelength generated by the second laser input and provides a second electronic signal. A third surface optical signal analyzer receives a third light signal at a sum-frequency wavelength generated by the first laser input and the second laser input on the semiconductor wafer to be interrogated and converts the light signal to a third electronic signal. An electronic signal analyzer compares the first, second and third electronic signals for determining the level of semiconductor wafer contamination.

26 Claims, 1 Drawing Sheet

NONLINEAR OPTICAL SYSTEM FOR SENSING THE PRESENCE OF CONTAMINATION ON A SEMICONDUCTOR WAFER

BACKGROUND OF THE INVENTION

1. Field of the Invention

The present invention relates to monitoring contamination on semiconductor wafers and more particularly to the use of second-order nonlinear optics to determine the level of contamination with a high degree of specificity.

2. Description of the Related Art

In nonlinear optics, outputs are produced at sum, difference or harmonic frequencies of the input(s). Using second order nonlinear optical surface spectroscopy to examine the physical properties and behavior of a surface or interface was originally proposed in the 1960's, in "Light Waves at the Boundary of Nonlinear Media" by Bloembergen and P. S. Pershan, The Physical Review, 128, Page 193 (1962). Experimental work involving second harmonic generation was also performed. However, because lasers at the time were comparatively feeble, impractical, slow, etc., there was little subsequent work done on the development of second harmonic generation or, more generally, second order nonlinear optical (NLO) processes at surfaces until considerably later.

Recently, researchers have reviewed NLO processing and concluded that lasers had developed enough that they could be used for studying the physical and chemical properties of surfaces and interfaces. For example, a theoretical study of the physics of the interface, and not its engineering aspects, has been performed. See Journal of Vacuum Science and Technology B, Volume 3, Number 5, September October 1985, Pages 1464–1466, Y. R. Shen, "Surface Studies by Optical Second Harmonic Generation: an Overview."

In U.S. Pat. No. 5,294,289, T. F. Heinz et al. discuss the use of second harmonic generation as a means to monitor the epitaxial growth of silicon semiconductor structures in a high vacuum chamber. Specifically, they examined the spectroscopic response at the interface between the electronically active silicon and the insulative layer of calcium fluoride. By monitoring the magnitude of the resonance, they could ascertain whether the insulator was present on the surface and whether it had electronically binded to the underlying semiconductor. The system that is used examines the total intensity only of the second harmonic light that is generated and there is no discussion of calibration against other signals produced at the surface. There is also no discussion of the use of second harmonic generation (SHG) for the detection of contamination.

In U.S. Pat. No. 5,623,341, J. H. Hunt discusses the use of sum-frequency generation for the detection of contamination and corrosion on engine parts. In this incarnation, one of the inputs is a tunable IR beam that is tuned to a resonance of the contamination on the surface. The efficiency of the sum-frequency process is increased (so-called resonant enhancement) when the IR beam is resonant with a contaminant. If the contaminant is not present, there is no resonant enhancement. By comparing on and off resonant signals, the presence and level of contaminant can be deduced. However, there is no discussion of application to semiconductor materials. Given that the nonlinear optical response of metal and semiconductor are quite different, one cannot assume that the diagnostic is useful in the other environment.

In U.S. Pat. No. 5,875,029, P. C. Jann et al. describe a versatile optical inspection instrument and method to inspect magnetic disk surfaces for surface defects. The device provides surface position information of the defects. However, the technique involves only linear optical processes. That is, the input and output light wavelengths are the same. There is also no discussion of contamination.

In U.S. Pat. No. 5,883,714, Jann et al. describe a versatile optical inspection instrument and method to inspect magnetic disk surfaces for surface defects. The device is based on interferometric measurement and detects contaminants by measuring the Doppler shift in the light that results from scanning the light onto a contaminant or defect. By scanning, the device provides surface position information of the defects. However, the technique involves only linear optical processes and senses only phase changes. That is, the input and output light wavelengths are the same and there is no discussion of contamination.

In U.S. Pat. No. 5,898,499, J. L. Pressesky discusses a system for detecting local surface discontinuities in magnetic storage discs. The device is an interferometric detector which scans the disc in a spiral motion. Local defects cause local changes in phase which are measured by interferometric techniques. This is a linear optical technique.

In U.S. Pat. No. 5,932,423, T. Sawatari et al. discuss a scatterometer for detecting surface defects in semiconductor wafers. This device is a linear interferometric device.

In U.S. Pat. No. 5,973,778, J. H. Hunt discusses the use of second harmonic generation for investigating molecular alignment within a thin polyimide film. The technique uses changes in the second harmonic polarization to determine surface molecular alignment. There is no discussion of semiconductor materials, or contamination. The nonlinear optical response of a semiconductor will be quite different than that of a liquid crystal film.

In U.S. Pat. No. 6,317,514 B1, S. Reinhorn et al. discuss a method and apparatus for inspecting a wafer surface to detect the presence of conductive material on the wafer. The device uses UV initiated electron emission to determine the location of conductive areas. Those areas which are metal will emit electrons. If the area, which is supposed to be conductive, is not, there will be no electron emission.

In U.S. Pat. No. 6,359,451 B1, G. N. Wallmark discusses a system for testing for opens and shorts between conductor traces on a circuit board. The technique uses electron scattering to perform its diagnostics and has no optics associated with it.

SUMMARY

In a broad aspect, the optical system of the present invention includes a first optical source for providing a first laser input directable to a location on a semiconductor wafer to be interrogated. A second optical source provides a second laser input directable to the semiconductor wafer location to be interrogated. The first and second laser inputs are alignable so that their surface locations of optical illumination overlap on the interrogated location. A first surface optical signal analyzer receives a first light signal at a first second-harmonic wavelength generated by the first laser input on the semiconductor wafer to be interrogated. The first surface optical signal analyzer converts the first light signal at the first second-harmonic wavelength to a first electronic signal, thus monitoring the intensity of the first second-harmonic wavelength, as a function of semiconductor wafer contamination. A second surface optical signal analyzer receives a second light signal at a second second-harmonic wavelength generated by the second laser input on the semiconductor wafer to be interrogated. The second surface optical signal analyzer converts the second light signal at the second second-harmonic wavelength to a second electronic signal, thus monitoring the intensity of the second second-harmonic wavelength, as a function of semiconductor wafer contamination. A third surface optical signal analyzer receives a third light signal at a sum-frequency wavelength generated by the first laser input and the second laser input on the semiconductor wafer to be interrogated. The third surface optical signal analyzer converts the third light signal at the sum-frequency wavelength to a third electronic signal, thus monitoring the intensity of the sum-frequency wavelength, as a function of semiconductor wafer contamination. An electronic signal analyzer compares the first, second and third electronic signals for determining the level of semiconductor wafer contamination.

Other objects, advantages, and novel features will become apparent from the following detailed description of the invention when considered in conjunction with the accompanying drawings.

DETAILED DESCRIPTION OF THE INVENTION

Figure 1:
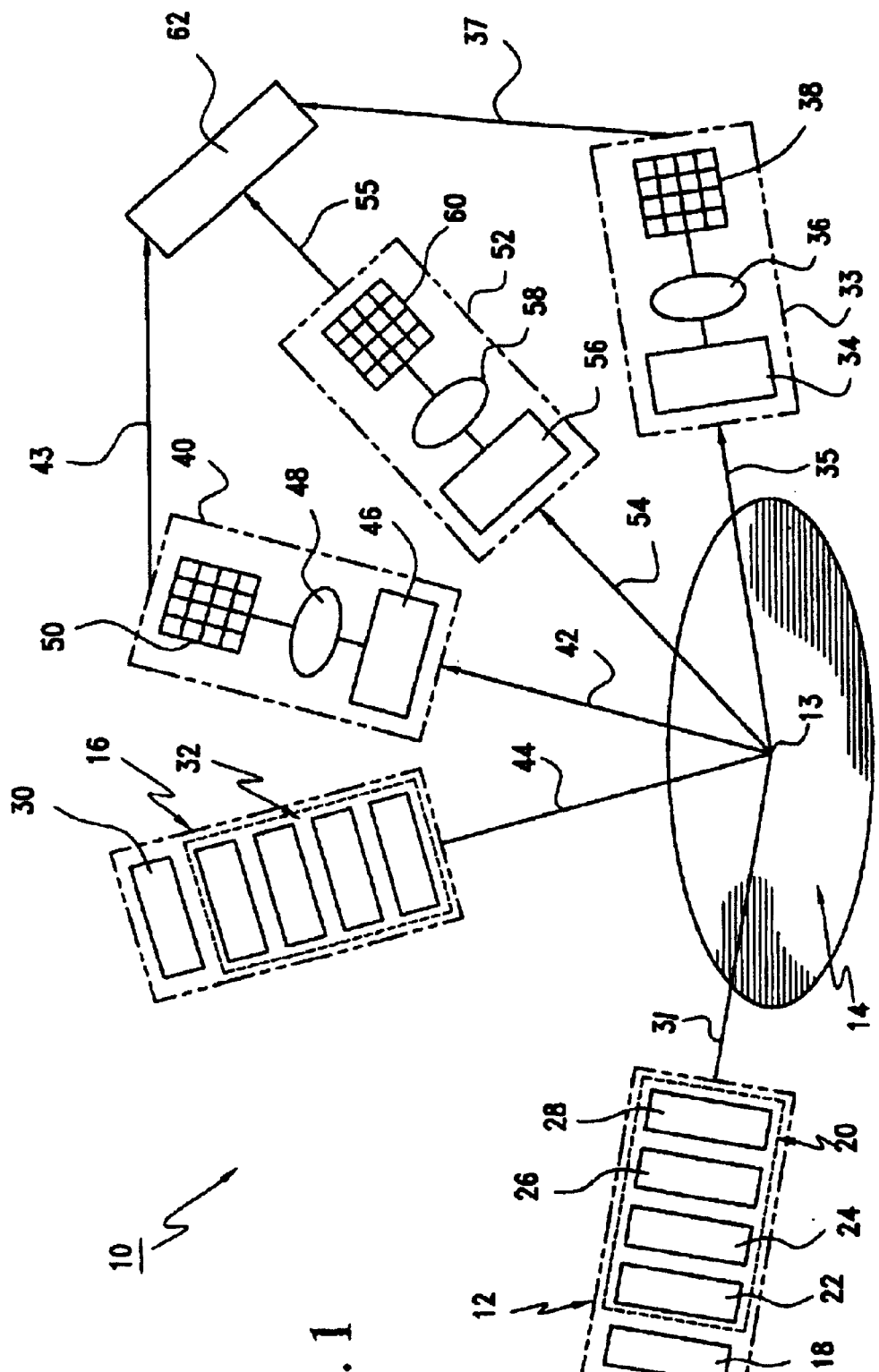
FIG. 1 is a schematic representation of the nonlinear optical system of the present invention.

Referring now to the drawings and the characters of reference marked thereon, FIG. 1 illustrates a preferred embodiment of the nonlinear optical system of the present invention, designated generally as 10. Diagnostic system 10 includes a first optical source, indicated by phantom lines 12 for providing a first laser input that is directable to a location 13 on a surface 14 of the semiconductor wafer to be interrogated. A second optical source 16 provides a second laser input that is also directable to the location 13 on the surface 14 to be interrogated. The optical sources 12, 16 are aligned so that their surface areas of optical illumination overlap on the interrogated surface 14. This alignment may be implemented via a series of refractive and reflective elements. For example, by changing their tilt in two axes, two mirrors in series can propagate a laser beam to any position on a surface.

The first optical source 12 includes a laser 18 in optical communication with an associated input optics 20. The laser 18 may be, for example, a pulsed diode laser, a continuous wave diode laser or a solid state laser. In certain applications, the laser wavelength may be fixed and in others it may be tunable. The input optics 20 preferably includes an input polarizer 22, an input wavelength discriminator 24, an input spatial filter 26 and an input propagation optics 28. The input polarizer 22 could be a brewster angle polarizer, a thin film polarizer, a Glan-air or Glan-Thompson polarizer or other crystal polarizer. The wavelength discriminator may be, for example, a color filter, a dielectric film, a holographic transmission filter, or a grating. The input propagation optics 28 could be formed of one or more refractive or reflective optics which, when used in combination, control the divergence or convergence of the beam as it propagates towards the surface.

The second optical source 16 also includes a laser 30 and associated input optics 32, that may be as described above with respect to the first optical source 12. However, the optics 32 is optimized for the wavelength of the second optical source 16.

A first surface optical signal analyzer 33 receives a first light signal 35 at a first second-harmonic wavelength generated by the first laser input 31 on the semiconductor wafer to be interrogated. The first surface optical signal analyzer 33 converts the first light signal 35 at the first second-harmonic wavelength to a first electronic signal 37, thus monitoring the intensity of the first second-harmonic wavelength, as a function of semiconductor wafer contamination. The analyzer 33 includes a first output wavelength discriminator 34 that receives the reflection of the first laser input 31 from the interrogated surface 14. The first output wavelength discriminator 34 is transmissive at the first second-harmonic wavelength and substantially non-transmissive at wavelengths longer than the first second-harmonic wavelength. The first output wavelength discriminator 34, like the input discriminator, may comprise a color filter, a dielectric film, a holographic transmission filter, or a grating.

First signal collection optics 36 receives an output of the wavelength discriminator 34 and directs the propagation of the output so that a first collected optical light signal is formed after propagation through the first signal collection optics 36. The first signal collection optics 36 may be either refractive or reflective optics which, when used in conjunction, act to control the divergence of the light coming from the surface so that as much of the first signal, as is technically possible, is collected for subsequent analysis.

A first optical detector 38 converts the first collected optical light signal to the first electronic signal 37, thus monitoring the intensity of the first second-harmonic wavelength, as a function of semiconductor wafer contamination. This may be, for example, an avalanche photodiode which creates an electronic signal proportional to the amount of light incident on it.

A second surface optical signal analyzer 40 receives a second light signal 42 at a second harmonic wavelength generated by the second laser input 44 on the semiconductor wafer to be interrogated. The second surface optical signal analyzer 40 converts the second light signal 42 at the second second-harmonic wavelength to a second electronic signal 43, thus monitoring the intensity of the second second-harmonic wavelength, as a function of semiconductor wafer contamination. The analyzer 40 includes a second output wavelength discriminator 46 that receives the reflection of the second laser input 44 from the interrogated surface 14. The second output wavelength discriminator 46 is transmissive at the second second-harmonic wavelength and substantially non-transmissive at wavelengths longer than the second second-harmonic wavelength. The second output wavelength discriminator 46, like the input and output discriminators, may comprise a color filter, a dielectric film, a holographic transmission filter or a grating.

Second signal collection optics 48 receives an output of the wavelength discriminator 46 and directs the propagation of the output so that a second collected optical light signal is formed after propagation through the second signal collection optics. The second signal collection optics 48 may be either refractive or reflective optics which, when used in conjunction, act to control the divergence of the light coming from the surface so that as much of the second signal, as is technically possible, is collected for subsequent analysis.

A second optical detector 50 converts the second collected optical light signal to the second electronic signal 43, thus monitoring the intensity of the second second-harmonic wavelength, as a function of semiconductor wafer contamination. As was the first optical detector 38, the second optical detector 50 may be, for example, an avalanche photodiode, which creates an electronic signal proportional to the amount of light incident on it.

A third surface optical signal analyzer 52 receives a third light signal 54 at a sum-frequency wavelength generated by the first laser input 31 and the second laser input 44 on the semiconductor wafer to be interrogated. The third surface optical signal analyzer 52 converts the third light signal 54 at the sum-frequency wavelength to a third electronic signal 55, thus monitoring the intensity of the sum-frequency wavelength, as a function of semiconductor wafer contamination. The analyzer 52 includes a third output wavelength discriminator 56 that receives the reflection of the third light signal 54 from the interrogated surface 14. The third output wavelength discriminator 56 is transmissive at the sum-frequency wavelength and substantially non-transmissive at wavelengths longer than the sum-frequency wavelength. As in the other instances, the wavelength discriminator 56 may comprise a color filter, a dielectric film, a holographic transmission filter or a grating.

Third signal collection optics 58 receives an output of the wavelength discriminator 56 and directs the propagation of the output so that a third collected optical light signal is formed after propagation through the third signal collection optics. The third signal collection optics 58 may be either refractive or reflective optics which, when used in conjunction, act to control the divergence of the light coming from the surface so that as much of the third light signal, as is technically possible, is collected for subsequent analysis.

A third optical detector 60 converts the third collected optical light signal to the third electronic signal 55, thus monitoring the intensity of the sum-frequency wavelength, as a function of semiconductor wafer contamination. As in the other instances, the third optical detector 60 may be, for example, an avalanche photodiode, which creates an electronic signal proportional to the amount of light incident on it.

An electronic signal analyzer 62 compares the first, second and third electronic signals 37, 43, 55 for determining the level of semiconductor wafer contamination. The electronic signal analyzer 62 may be, for example, a computer with suitable internal electronics to acquire the first, second and third electronics signals and to implement the appropriate mathematical algorithms to interpret the signals.

The wavelength selection of the first optical source and second optical source may be chosen so that the wavelength of one will coincide with surface contamination absorption features while the other will not. This choice is made so that either the first or second electronic signal will have a spectroscopic response to the contamination, while the other will not. The third electronic signal, being produced by sum-frequency, will also contain a resonant response, but its response will be different from that produced by the second harmonic leading to the first and second electronic signals. Suitable algorithmic comparisons are performed with the first, second and third electronic signals.

The use of the described system allows the user to perform contamination measurements on a semiconductor wafer with a very high degree of sensitivity. As the semiconductor industry moves to increase production speeds and yields, it is increasingly important to perform inspections in an in-situ fashion. Additionally, the thin active semiconductor regions which are used place ever tighter restrictions on the level of contamination that is allowable. Furthermore, the described technique allows the user to make the distinction between contamination and surface defects by comparison between signals containing resonant responses and those which do not. A surface sensitive optical characterization of semiconductor wafer contamination has not previously been described.

In a preferred embodiment, the first optical source may comprise a Nd:YAG laser operating on the 1.064 micron line or a Nd:YAG laser and a harmonic converter for operation at the second or third harmonic of the laser fundamental output wavelength. It may operate with a maximum pulse length of 10 nanoseconds. The optimal pulse length is less than 1 picosecond.

The input optics of the first optical source preferably includes a steering apparatus comprising two mirrors aligned so that that their surface normals are non-coplanar. It also preferably includes a polarization rotator comprising a half-wave plate. The half-wave plate should be optimized for an output wavelength of the input laser. The input optics also preferably uses a linear polarizer that is aligned so that an output wavelength is p or s polarized with the polarization referenced to the surface to be interrogated. A spot shaping apparatus is used, comprising a series of lenses, for creating a controlled spot size on the surface to be interrogated. Finally, a narrow band optical filter is used that passes only an output wavelength or harmonic wavelength of the input laser.

In this preferred embodiment, the second optical source preferably comprises a tunable IR input—an optical parametric oscillator and amplifier tunable output in a band of 1.5–10 microns. The internal optical resonator configuration of the optical parametric oscillator will be configured in such a manner as to broaden the bandwidth of the second optical source to cover all of the infrared wavelengths of interest to the specific application. A steering apparatus is utilized including two mirrors aligned so that their surface normals are non-coplanar, with the mirrors' reflectances being optimized for an output wavelength of the infrared laser. A polarization rotator is used that is operative in the infrared range. A linear polarizer is used and is aligned so that an output wavelength is p or s polarized with the polarization referenced to the surface to be interrogated. Again, a spot shaping apparatus is used, including a series of lenses for creating a controlled spot size on the surface to be interrogated, the lenses being transparent in the infrared range. Finally, an optical filter is utilized including a semiconductor crystal having a bandgap that passes infrared, but blocks shorter wavelengths.

The output wavelength discriminator preferably includes an iris; a filter in optical communication with the iris for passing the sum frequency wavelength; and, a linear polarizer in optical communication with the filter, aligned to detect either the p or s polarized sum-frequency wavelength, wherein the polarization is referenced to the surface where the sum-frequency light is generated.

The signal collection optics preferably includes a telescope system comprising a plurality of telescope system lenses having coatings optimized for the sum frequency. The detector preferably comprises an avalanche photodiode, being electronically gated to only detect output light generated by the input laser pulses. A computer collects and analyzes the electronic data from the detector.

Obviously, many modifications and variations of the present invention are possible in light of the above teachings. It is, therefore, to be understood that within the scope of the appended claims, the invention may be practiced otherwise than as specifically described.

What is claimed and desired to be secured by Letters Patent of the United States is:

1. A nonlinear optical system for sensing the presence of contamination on a semiconductor wafer, comprising:
   a) a first optical source for providing a first laser input directable to a location on a semiconductor wafer to be interrogated;
   b) a second optical source for providing a second laser input directable to said semiconductor wafer location to be interrogated, said first and second laser inputs being alignable so that their surface locations of optical illumination overlap on said interrogated location;
   c) a first surface optical signal analyzer for receiving a first light signal at a first second-harmonic wavelength generated by said first laser input on the semiconductor wafer to be interrogated, said first surface optical signal analyzer for converting said first light signal at the first second-harmonic wavelength to a first electronic signal, thus monitoring the intensity of said first second-harmonic wavelength, as a function of semiconductor wafer contamination;
   d) a second surface optical signal analyzer for receiving a second light signal at a second second-harmonic wavelength generated by said second laser input on the semiconductor wafer to be interrogated, said second surface optical signal analyzer for converting said second light signal at the second second-harmonic wavelength to a second electronic signal, thus monitoring the intensity of said second second-harmonic wavelength, as a function of semiconductor wafer contamination;
   e) a third surface optical signal analyzer for receiving a third light signal at a sum-frequency wavelength generated by said first laser input and said second laser input on the semiconductor wafer to be interrogated, said third surface optical signal analyzer for converting said third light signal at said sum-frequency wavelength to a third electronic signal, thus monitoring the intensity of said sum-frequency wavelength, as a function of semiconductor wafer contamination; and,
   f) an electronic signal analyzer for comparing said first, second and third electronic signals for determining the level of semiconductor wafer contamination.

2. The nonlinear optical system of claim 1, wherein said first surface optical signal analyzer, comprises:
   a) a first output wavelength discriminator for receiving said first light signal at the first second-harmonic wavelength generated by said first laser input on the semiconductor wafer to be interrogated, said first output wavelength discriminator being transmissive at said first second-harmonic wavelength and substantially non-transmissive at wavelengths longer than the first second-harmonic wavelength;
   b) a first signal collection optics for receiving an output of said first output wavelength discriminator and directing the propagation of said output so that a first collected optical light signal is formed after propagation through said first signal collection optics; and,
   c) a first optical detector for converting said first collected optical light signal to said first electronic signal, thus monitoring the intensity of said first second-harmonic wavelength, as a function of semiconductor wafer contamination.

3. The nonlinear optical system of claim 1, wherein said second surface optical signal analyzer, comprises:

a) a second output wavelength discriminator for receiving said second light signal at the second second-harmonic wavelength generated by said second laser input on the semiconductor wafer to be interrogated, said second output wavelength discriminator being transmissive at said second second-harmonic wavelength and substantially non-transmissive at wavelengths longer than the second second-harmonic wavelength;
   b) a second signal collection optics for receiving an output of said second output wavelength discriminator and directing the propagation of said output so that a second collected optical light signal is formed after propagation through said second signal collection optics; and,
   c) a second optical detector for converting said second collected optical light signal to said second electronic signal, thus monitoring the intensity of said second second-harmonic wavelength, as a function of semiconductor wafer contamination.

4. The nonlinear optical system of claim 1, wherein said third surface optical signal analyzer, comprises:
   a) a third output wavelength discriminator for receiving said third light signal at the sum-frequency wavelength generated by said first laser input and said second laser input on the semiconductor water to be interrogated, said third output wavelength discriminator being transmissive at said sum-frequency wavelength and substantially non-transmissive at wavelengths longer than the sum-frequency wavelength;
   b) a third signal collection optics for receiving an output of said third output wavelength discriminator and directing the propagation of said output so that a third collected optical light signal is formed after propagation through said third signal collection optics; and,
   c) a third optical detector for converting said third collected optical light signal to said third electronic signal, thus monitoring the intensity of said sum-frequency wavelength, as a function of semiconductor wafer contamination.

5. The nonlinear optical system of claim 1, wherein said electronic analyzer comprises a computer having electronics for acquiring said first, second and third electronic signals.

6. The nonlinear optical system of claim 1, wherein said first optical source comprises a first laser in optical communication with a first input optics.

7. The nonlinear optical system of claim 1, wherein said first optical source comprises a first laser in optical communication with a first input optics, said first input optics comprising a first input polarizer, a first input wavelength discriminator, a first input spatial filter and first input propagation optics in optical communication.

8. The nonlinear optical system of claim 1, wherein said second optical source comprises a second laser in optical communication with a second input optics.

9. The nonlinear optical system of claim 1, wherein said second optical source comprises a second laser in optical communication with a second input optics, said second input optics comprising a second input polarizer, a second input wavelength discriminator, a second input spatial filter and second input propagation optics in optical communication.

10. The nonlinear optical system of claim 1, wherein said first optical source comprises a pulsed diode laser.

11. The nonlinear optical system of claim 1, wherein said first optical source comprises a Nd:YAG laser operating on the 1.064 micron line.

12. The nonlinear optical system of claim 1, wherein said first optical source comprises a Nd:YAG laser and a harmonic converter for operation at the second or third harmonic of the laser fundamental output wavelength.

13. The nonlinear optical system of claim 1, wherein said first optical source comprises a Nd:YAG laser operating on the 1.064 micron line and a maximum pulse length of 10 nanoseconds.

14. The nonlinear optical system of claim 1, wherein said first optical source comprises a Nd:YAG laser operating on the 1.064 micron line and a pulse length of less than 1 picosecond.

15. A nonlinear optical system for sensing the presence of contamination on a semiconductor wafer, comprising:
   a) first optical source for providing a first laser input directable to a location on a semiconductor wafer to be interrogated;
   b) a second optical source for providing a second laser input directable to said semiconductor wafer location to be interrogated, said first and second laser inputs being alignable so that their surface locations of optical illumination overlap on said interrogated location;
   c) a first output wavelength discriminator for receiving a first light signal at the first second-harmonic wavelength generated by said first laser input on the semiconductor wafer to be interrogated, said first output wavelength discriminator being transmissive at said first second-harmonic wavelength and substantially non-transmissive at wavelengths longer than the first second-harmonic wavelength;
   d) a first signal collection optics for receiving an output of said first output wavelength discriminator and directing the propagation of said output so that a first collected optical light signal is formed after propagation through said first signal collection optics;
   e) a first optical detector for converting said first collected optical light signal to a first electronic signal, thus monitoring the intensity of said first second-harmonic wavelength, as a function of semiconductor wafer contamination;
   f) a second output wavelength discriminator for receiving a second light signal at the second second-harmonic wavelength generated by said second laser input on the semiconductor wafer to be interrogated, said second output wavelength discriminator being transmissive at said second second-harmonic wavelength and substantially non-transmissive at wavelengths longer than the second second-harmonic wavelength;
   g) a second signal collection optics for receiving an output of said second output wavelength discriminator and directing the propagation of said output so that a second collected optical light signal is formed after propagation through said second signal collection optics;
   h) a second optical detector for converting said second collected optical light signal to a second electronic signal, thus monitoring the intensity of said second second-harmonic, as a function of semiconductor wafer contamination;
   i) a third output wavelength discriminator for receiving a third light signal at the sum-frequency wavelength generated by said first laser input and said second laser input on the semiconductor wafer to be interrogated, said third output wavelength discriminator being transmissive at said sum-frequency wavelength and substantially non-transmissive at wavelengths longer than the sum-frequency wavelength;
   j) a third signal collection optics for receiving an output of said third output wavelength discriminator and directing the propagation of said output so that a third collected optical light signal is formed after propagation through said third signal collection optics;
   k) a third optical detector for converting said third collected optical light signal to a third electronic signal, thus monitoring the intensity of said sum-frequency wavelength, as a function of semiconductor wafer contamination; and,
   l) an electronic signal analyzer for comparing said first, second and third electronic signals for determining the level of semiconductor wafer contamination.

16. The nonlinear optical system of claim 15, wherein said first optical source comprises a pulsed diode laser.

17. The nonlinear optical system of claim 15, wherein said first optical source comprises a Nd:YAG laser operating on the 1.064 micron line.

18. The nonlinear optical system of claim 15, wherein said first optical source comprises a Nd:YAG laser and a harmonic converter for operation at the second or third harmonic of the laser fundamental output wavelength.

19. A method for sensing the presence of contamination on a semiconductor wafer, comprising the steps of:
   a) directing a first laser input to a location on a semiconductor wafer to be interrogated;
   b) directing a second laser input to said location on a semiconductor wafer to be interrogated, said first and second laser inputs being aligned so that their surface locations of optical illumination overlap on said interrogated location;
   c) receiving a first light signal at a first second-harmonic wavelength generated by said first laser input on the semiconductor wafer to be interrogated, via a first surface optical signal analyzer, said first surface optical signal analyzer for converting said first light signal at the first second-harmonic wavelength to a first electronic signal, thus monitoring the intensity of said first second-harmonic wavelength, as a function of semiconductor wafer contamination;
   d) receiving a second light signal at a second second-harmonic wavelength generated by said second laser input on the semiconductor wafer to be interrogated, via a second surface optical signal analyzer, said second surface optical signal analyzer for converting said second light signal at the second second-harmonic wavelength to a second electronic signal, thus monitoring the intensity of said second second-harmonic wavelength, as a function of semiconductor wafer contamination;
   e) receiving a third light signal at a sum-frequency wavelength generated by said first laser input and said second laser input on the semiconductor wafer to be interrogated, via a third surface optical signal analyzer, said third surface optical signal analyzer for converting said third light signal at the sum-frequency wavelength to a third electronic signal, thus monitoring the intensity of said sum-frequency wavelength, as a function of semiconductor wafer contamination; and,
   f) comparing said first, second and third electronic signals for determining the level of semiconductor wafer contamination.

20. The method of claim 19, wherein said step of directing a first laser input comprises directing a pulsed diode laser.

21. The method of claim 19, wherein said step of directing a first laser input comprises directing a Nd:YAG laser operating on the 1.064 micron line.

22. The method of claim 19, wherein said step of directing a first laser input comprises directing a Nd:YAG laser operating on the 1.064 micron line and a maximum pulse length of 10 nanoseconds.

23. The method of claim 19, wherein said step of directing a first laser input comprises directing a Nd:YAG laser operating on the 1.064 micron line and a pulse length of less than 1 picosecond.

24. The method of claim 19, wherein said step of receiving a first light signal at a first second-harmonic wavelength generated by said first laser input on the semiconductor wafer to be interrogated, comprises the steps of:
   a) receiving said first light signal at the first second-harmonic wavelength generated by said first laser input on the semiconductor wafer to be interrogated, via a first output wavelength discriminator, said first output wavelength discriminator being transmissive at said first second-harmonic wavelength and substantially non-transmissive at wavelengths longer than the first second-harmonic wavelength;
   b) receiving an output of said first output wavelength discriminator and directing the propagation of said output, via a first signal collection optics, so that a first collected optical light signal is formed after propagation through said first signal collection optics; and,
   c) converting said first collected optical light signal to said first electronic signal, via a first optical detector, thus monitoring the intensity of said first second-harmonic wavelength, as a function of semiconductor wafer contamination.

25. The method of claim 19, wherein said step of receiving a second light signal at a second second-harmonic wavelength generated by said first laser input on the semiconductor wafer to be interrogated, comprises the steps of:
   a) receiving said second light signal at the second second-harmonic wavelength generated by said first laser input on the semiconductor wafer to be interrogated, via a second output wavelength discriminator, said second output wavelength discriminator being transmissive at said second second-harmonic wavelength and substantially non-transmissive at wavelengths longer than the second second-harmonic wavelength;
   b) receiving an output of said second output wavelength discriminator and directing the propagation of said output, via a second signal collection optics, so that a second collected optical light signal is formed after propagation through said second signal collection optics; and,
   c) converting said second collected optical light signal to said first electronic signal, via a second optical detector, thus monitoring the intensity of said second second-harmonic wavelength, as a function of semiconductor wafer contamination.

26. The method of claim 19, wherein said step of receiving a third light signal at a sum-frequency wavelength generated by said first laser input and said second laser input on the semiconductor wafer to be interrogated, comprises the steps of:
   a) receiving said third light signal at the sum-frequency wavelength generated by said first and second laser inputs on the semiconductor wafer to be interrogated, via a third output wavelength discriminator, said third output wavelength discriminator being transmissive at said sum-frequency wavelength and substantially non-transmissive at wavelengths longer than the sum-frequency wavelength;
   b) receiving an output of said third output wavelength discriminator and directing the propagation of said output, via a third signal collection optics, so that a third collected optical light signal is formed after propagation through said third signal collection optics; and,
   c) converting said third collected optical light signal to said third electronic signal, via a third optical detector, thus monitoring the intensity of said sum-frequency wavelength, as a function of semiconductor wafer contamination.

* * * * *